United States Patent
Henley et al.

(10) Patent No.: US 10,084,944 B2
(45) Date of Patent: Sep. 25, 2018

(54) CARD EDGE CONNECTOR FOR AN IMAGING SENSOR

(71) Applicant: Depuy Synthes Products, Inc., Raynham, MA (US)

(72) Inventors: Jeremiah D. Henley, Salt Lake City, UT (US); Laurent Blanquart, Westlake Village, CA (US); Brian Dean, Salt Lake City, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 576 days.

(21) Appl. No.: 14/666,210

(22) Filed: Mar. 23, 2015

(65) Prior Publication Data
US 2015/0271370 A1    Sep. 24, 2015

Related U.S. Application Data

(60) Provisional application No. 61/968,959, filed on Mar. 21, 2014.

(51) Int. Cl.
| | |
|---|---|
| A61B 1/04 | (2006.01) |
| H04N 5/225 | (2006.01) |
| A61B 1/00 | (2006.01) |
| A61B 1/05 | (2006.01) |

(52) U.S. Cl.
CPC ....... *H04N 5/2253* (2013.01); *A61B 1/00124* (2013.01); *A61B 1/051* (2013.01); *H04N 5/2256* (2013.01); *H04N 2005/2255* (2013.01)

(58) Field of Classification Search
None
See application file for complete search history.

(56) References Cited

U.S. PATENT DOCUMENTS

| | | |
|---|---|---|
| 3,666,885 A | 5/1972 | Hemsley et al. |
| 4,011,403 A | 3/1977 | Epstein et al. |
| 4,363,963 A | 12/1982 | Ando |
| 4,433,675 A | 2/1984 | Konoshima |
| 4,436,095 A | 3/1984 | Kruger |
| 4,473,839 A | 9/1984 | Noda |
| 4,644,403 A | 2/1987 | Sakai et al. |
| 4,651,226 A | 3/1987 | Motoori et al. |
| 4,692,606 A | 9/1987 | Sakai et al. |
| 4,740,837 A | 4/1988 | Yanagisawa et al. |
| 4,741,327 A | 5/1988 | Yabe |

(Continued)

FOREIGN PATENT DOCUMENTS

| | | |
|---|---|---|
| CN | 1520696 A | 8/2004 |
| CN | 101079966 A | 11/2007 |

(Continued)

OTHER PUBLICATIONS

Blumenfeld, et al. Three-dimensional image registration of MR proximal femur images for the analysis of trabecular bone parameters. Oct. 2008. [retrieved on Jul. 30, 2014] Retrieved from the internet: <URL: http://www.ncbi.nlm.nih.gov/pmc/articles/PMC2673590/>.

*Primary Examiner* — Nhon Diep
(74) *Attorney, Agent, or Firm* — Terrence J. Edwards; TechLaw Ventures, PLLC

(57) ABSTRACT

The disclosure extends to devices, systems and methods for connecting one or more sensors to one or more printed circuit boards (PCB) in the distal end or tip of a scope. The disclosure also extends to a connector assembly for an image sensor for protecting the sensor and conveying information from the sensor to the PCB.

28 Claims, 10 Drawing Sheets

(56) References Cited

U.S. PATENT DOCUMENTS

| | | |
|---|---|---|
| 4,742,388 A | 5/1988 | Cooper et al. |
| 4,745,471 A | 5/1988 | Takamura et al. |
| 4,773,396 A | 9/1988 | Okazaki |
| 4,782,386 A | 11/1988 | Ams et al. |
| 4,786,965 A | 11/1988 | Yabe |
| 4,832,003 A | 5/1989 | Yabe |
| 4,845,555 A | 7/1989 | Yabe et al. |
| 4,853,772 A | 8/1989 | Kikuchi |
| 4,853,773 A | 8/1989 | Hibino et al. |
| 4,866,526 A | 9/1989 | Ams et al. |
| 4,884,133 A | 11/1989 | Kanno et al. |
| 4,884,134 A | 11/1989 | Tsuji et al. |
| 4,918,521 A | 5/1990 | Yabe et al. |
| 4,924,856 A | 5/1990 | Noguchi |
| 4,938,205 A | 7/1990 | Nudelman |
| 4,942,473 A | 7/1990 | Zeevi et al. |
| 4,947,246 A | 8/1990 | Kikuchi |
| 4,953,539 A | 9/1990 | Nakamura et al. |
| 4,959,710 A | 9/1990 | Uehara et al. |
| 5,001,556 A | 3/1991 | Nakamura et al. |
| 5,016,975 A | 5/1991 | Sasaki et al. |
| 5,021,888 A | 6/1991 | Kondou et al. |
| 5,047,846 A | 9/1991 | Uchiyama et al. |
| RE33,854 E | 3/1992 | Adair |
| 5,103,497 A | 4/1992 | Hicks |
| 5,111,804 A | 5/1992 | Funakoshi |
| 5,133,035 A | 7/1992 | Hicks |
| 5,187,572 A | 2/1993 | Nakamura et al. |
| 5,188,094 A | 2/1993 | Adair |
| 5,196,938 A | 3/1993 | Blessinger |
| 5,200,838 A | 4/1993 | Nudelman et al. |
| 5,220,198 A | 6/1993 | Tsuji |
| 5,228,430 A | 7/1993 | Sakamoto |
| 5,233,416 A | 8/1993 | Inoue |
| 5,241,170 A | 8/1993 | Field, Jr. et al. |
| 5,264,925 A | 11/1993 | Shipp et al. |
| 5,313,306 A | 5/1994 | Kuban et al. |
| 5,325,847 A | 7/1994 | Matsuno |
| 5,365,268 A | 11/1994 | Minami |
| 5,402,768 A | 4/1995 | Adair |
| 5,408,268 A | 4/1995 | Shipp |
| 5,411,020 A | 5/1995 | Ito |
| 5,427,087 A | 6/1995 | Ito et al. |
| 5,454,366 A | 10/1995 | Ito et al. |
| 5,494,483 A | 2/1996 | Adair |
| 5,523,786 A | 6/1996 | Parulski |
| 5,550,595 A | 8/1996 | Hannah |
| 5,594,497 A | 1/1997 | Ahern et al. |
| 5,665,959 A | 9/1997 | Fossum et al. |
| 5,704,836 A | 1/1998 | Norton et al. |
| 5,730,702 A | 3/1998 | Tanaka et al. |
| 5,734,418 A | 3/1998 | Danna |
| 5,748,234 A | 5/1998 | Lippincott |
| 5,749,830 A | 5/1998 | Kaneko et al. |
| 5,754,313 A | 5/1998 | Pelchy et al. |
| 5,783,909 A | 7/1998 | Hochstein |
| 5,784,099 A | 7/1998 | Lippincott |
| 5,857,963 A | 1/1999 | Pelchy et al. |
| 5,887,049 A | 3/1999 | Fossum |
| 5,929,901 A | 7/1999 | Adair et al. |
| 5,949,483 A | 9/1999 | Fossum et al. |
| 5,986,693 A | 11/1999 | Adair et al. |
| 6,023,315 A | 2/2000 | Harrold et al. |
| 6,038,067 A | 3/2000 | George |
| 6,043,839 A | 3/2000 | Adair et al. |
| 6,139,489 A | 10/2000 | Wampler et al. |
| 6,142,930 A | 11/2000 | Ito et al. |
| 6,166,768 A | 12/2000 | Fossum et al. |
| 6,184,922 B1 | 2/2001 | Saito et al. |
| 6,184,940 B1 | 2/2001 | Sano |
| 6,215,517 B1 | 4/2001 | Takahashi et al. |
| 6,222,175 B1 | 4/2001 | Krymski |
| 6,239,456 B1 | 5/2001 | Berezin et al. |
| 6,272,269 B1 | 8/2001 | Naum |
| 6,275,255 B1 | 8/2001 | Adair et al. |
| 6,292,220 B1 | 9/2001 | Ogawa et al. |
| 6,294,775 B1 | 9/2001 | Seibel et al. |
| 6,310,642 B1 | 10/2001 | Adair et al. |
| 6,320,630 B1 | 11/2001 | Yamashita et al. |
| 6,331,156 B1 | 12/2001 | Haefele et al. |
| 6,389,205 B1 | 5/2002 | Muckner et al. |
| 6,416,463 B1 | 7/2002 | Tsuzuki et al. |
| 6,429,953 B1 | 8/2002 | Feng |
| 6,444,970 B1 | 9/2002 | Barbato |
| 6,445,022 B1 | 9/2002 | Barna et al. |
| 6,445,139 B1 | 9/2002 | Marshall et al. |
| 6,464,633 B1 | 10/2002 | Hosoda et al. |
| 6,466,618 B1 | 10/2002 | Messing et al. |
| 6,485,414 B1 | 11/2002 | Neuberger |
| 6,512,280 B2 | 1/2003 | Chen et al. |
| 6,567,115 B1 | 5/2003 | Miyashita et al. |
| 6,627,474 B2 | 9/2003 | Barna et al. |
| 6,631,230 B1 | 10/2003 | Campbell |
| 6,659,940 B2 | 12/2003 | Adler |
| 6,665,013 B1 | 12/2003 | Fossum et al. |
| 6,677,992 B1 | 1/2004 | Matsumoto et al. |
| 6,690,466 B2 | 2/2004 | Miller et al. |
| 6,692,431 B2 | 2/2004 | Kazakevich |
| 6,707,499 B1 | 3/2004 | Kung et al. |
| 6,772,181 B1 | 8/2004 | Fu et al. |
| 6,773,392 B2 | 8/2004 | Kikuchi et al. |
| 6,791,739 B2 | 9/2004 | Ramanujan et al. |
| 6,796,939 B1 | 9/2004 | Hirata et al. |
| 6,799,065 B1 | 9/2004 | Niemeyer |
| 6,809,358 B2 | 10/2004 | Hsieh et al. |
| 6,838,653 B2 | 1/2005 | Campbell et al. |
| 6,841,947 B2 | 1/2005 | Berg-johansen |
| 6,847,399 B1 | 1/2005 | Ang |
| 6,856,712 B2 | 2/2005 | Fauver et al. |
| 6,873,363 B1 | 3/2005 | Barna et al. |
| 6,879,340 B1 | 4/2005 | Chevallier |
| 6,899,675 B2 | 5/2005 | Cline et al. |
| 6,900,829 B1 | 5/2005 | Ozawa et al. |
| 6,906,745 B1 | 6/2005 | Fossum et al. |
| 6,921,920 B2 | 7/2005 | Kazakevich |
| 6,933,974 B2 | 8/2005 | Lee |
| 6,947,090 B2 | 9/2005 | Komoro et al. |
| 6,961,461 B2 | 11/2005 | MacKinnon et al. |
| 6,970,195 B1 | 11/2005 | Bidermann et al. |
| 6,977,733 B2 | 12/2005 | Denk et al. |
| 6,982,740 B2 | 1/2006 | Adair et al. |
| 6,999,118 B2 | 2/2006 | Suzuki |
| 7,009,634 B2 | 3/2006 | Iddan et al. |
| 7,009,648 B2 | 3/2006 | Lauxtermann et al. |
| 7,030,904 B2 | 4/2006 | Adair et al. |
| 7,037,259 B2 | 5/2006 | Hakamata et al. |
| 7,068,878 B2 | 6/2006 | Crossman-Bosworth et al. |
| 7,071,979 B1 | 7/2006 | Ohtani et al. |
| 7,079,178 B2 | 7/2006 | Hynecek |
| 7,102,682 B2 | 9/2006 | Baer |
| 7,105,371 B2 | 9/2006 | Fossum et al. |
| 7,106,377 B2 | 9/2006 | Bean et al. |
| 7,119,839 B1 | 10/2006 | Mansoorian |
| 7,151,568 B2 | 12/2006 | Kawachi et al. |
| 7,159,782 B2 | 1/2007 | Johnston et al. |
| 7,184,084 B2 | 2/2007 | Glenn |
| 7,189,226 B2 | 3/2007 | Auld et al. |
| 7,189,961 B2 | 3/2007 | Johnston et al. |
| 7,208,983 B2 | 4/2007 | Imaizumi et al. |
| 7,252,236 B2 | 8/2007 | Johnston et al. |
| 7,258,663 B2 | 8/2007 | Doguchi et al. |
| 7,261,687 B2 | 8/2007 | Yang |
| 7,280,139 B2 | 10/2007 | Pahr et al. |
| 7,298,938 B2 | 11/2007 | Johnston |
| 7,312,879 B2 | 12/2007 | Johnston |
| 7,319,478 B2 | 1/2008 | Dolt et al. |
| 7,355,155 B2 | 4/2008 | Wang |
| 7,356,198 B2 | 4/2008 | Chauville et al. |
| 7,365,768 B1 | 4/2008 | Ono et al. |
| 7,369,140 B1 | 5/2008 | King et al. |
| 7,369,176 B2 | 5/2008 | Sonnenschein et al. |
| 7,455,638 B2 | 11/2008 | Ogawa et al. |
| 7,470,229 B2 | 12/2008 | Ogawa et al. |
| 7,476,197 B2 | 1/2009 | Wiklof et al. |

(56) References Cited

U.S. PATENT DOCUMENTS

| | | |
|---|---|---|
| 7,532,760 B2 | 5/2009 | Kaplinsky et al. |
| 7,540,645 B2 | 6/2009 | Kazakevich |
| 7,544,163 B2 | 6/2009 | MacKinnon et al. |
| 7,545,434 B2 | 6/2009 | Bean et al. |
| 7,564,935 B2 | 7/2009 | Suzuki |
| 7,567,291 B2 | 7/2009 | Bechtel et al. |
| 7,573,516 B2 | 8/2009 | Krymski et al. |
| 7,573,519 B2 | 8/2009 | Phan et al. |
| 7,583,872 B2 | 9/2009 | Seibel et al. |
| 7,616,238 B2 | 11/2009 | Avni et al. |
| 7,630,008 B2 | 12/2009 | Sarwari |
| 7,744,528 B2 | 6/2010 | Wallace et al. |
| 7,783,133 B2 | 8/2010 | Dunki-Jacobs et al. |
| 7,784,697 B2 | 8/2010 | Johnston et al. |
| 7,791,009 B2 | 9/2010 | Johnston et al. |
| 7,792,378 B2 | 9/2010 | Liege et al. |
| 7,794,394 B2 | 9/2010 | Frangioni |
| 7,813,538 B2 | 10/2010 | Carroll et al. |
| 7,901,974 B2 | 3/2011 | Venezia et al. |
| 7,914,447 B2 | 3/2011 | Kanai |
| 7,916,193 B2 | 3/2011 | Fossum |
| 7,935,050 B2 | 5/2011 | Luanava et al. |
| 7,944,566 B2 | 5/2011 | Xie |
| 7,952,096 B2 | 5/2011 | Rhodes |
| 7,969,097 B2 | 6/2011 | Van De Ven |
| 7,995,123 B2 | 8/2011 | Lee et al. |
| 8,040,394 B2 | 10/2011 | Fossum et al. |
| 8,054,339 B2 | 11/2011 | Fossum et al. |
| 8,059,174 B2 | 11/2011 | Mann et al. |
| 8,100,826 B2 | 1/2012 | MacKinnon et al. |
| 8,159,584 B2 | 4/2012 | Iwabuchi et al. |
| 8,193,542 B2 | 6/2012 | Maehara |
| 8,212,884 B2 | 7/2012 | Seibel et al. |
| 8,231,522 B2 | 7/2012 | Endo et al. |
| 8,300,111 B2 | 10/2012 | Iwane |
| 8,372,003 B2 | 2/2013 | St. George et al. |
| 8,382,662 B2 | 2/2013 | Soper et al. |
| 8,396,535 B2 | 3/2013 | Wang et al. |
| 8,423,110 B2 | 4/2013 | Barbato et al. |
| 8,471,938 B2 | 6/2013 | Altice, Jr. et al. |
| 8,476,575 B2 | 7/2013 | Mokhnatyuk |
| 8,482,823 B2 | 7/2013 | Cheng |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,559,743 B2 | 10/2013 | Liege et al. |
| 8,582,011 B2 | 11/2013 | Dosluoglu |
| 8,602,971 B2 | 12/2013 | Farr |
| 8,605,177 B2 | 12/2013 | Rossi et al. |
| 8,610,808 B2 | 12/2013 | Prescher et al. |
| 8,614,754 B2 | 12/2013 | Fossum |
| 8,625,016 B2 | 1/2014 | Fossum et al. |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,836,834 B2 | 9/2014 | Hashimoto et al. |
| 8,848,063 B2 | 9/2014 | Jo et al. |
| 8,858,425 B2 | 10/2014 | Farr et al. |
| 8,885,034 B2 | 11/2014 | Adair et al. |
| 9,349,764 B1* | 5/2016 | Lee .................. H01L 27/14636 |
| 9,509,917 B2 | 11/2016 | Blanquart et al. |
| 9,516,239 B2 | 12/2016 | Blanquart et al. |
| 9,762,879 B2 | 9/2017 | Blanquart et al. |
| 9,777,913 B2 | 10/2017 | Talbert et al. |
| 2001/0017649 A1 | 8/2001 | Yaron |
| 2001/0030744 A1 | 10/2001 | Chang |
| 2001/0055462 A1 | 10/2001 | Seibel |
| 2002/0054219 A1 | 5/2002 | Jaspers |
| 2002/0064341 A1 | 5/2002 | Fauver et al. |
| 2002/0080248 A1 | 6/2002 | Adair et al. |
| 2002/0080359 A1 | 6/2002 | Denk et al. |
| 2002/0140844 A1 | 10/2002 | Kurokawa et al. |
| 2002/0158976 A1 | 10/2002 | Vni et al. |
| 2002/0158986 A1 | 10/2002 | Baer |
| 2003/0007087 A1 | 1/2003 | Hakamata et al. |
| 2003/0007686 A1 | 1/2003 | Roever |
| 2003/0107664 A1 | 6/2003 | Suzuki |
| 2003/0189663 A1 | 10/2003 | Dolt et al. |
| 2004/0082833 A1 | 4/2004 | Adler et al. |
| 2004/0170712 A1 | 9/2004 | Sadek El Mogy |
| 2005/0009982 A1 | 1/2005 | Inagaki et al. |
| 2005/0027164 A1 | 2/2005 | Barbato et al. |
| 2005/0038322 A1 | 2/2005 | Banik |
| 2005/0113641 A1 | 5/2005 | Bala |
| 2005/0122530 A1 | 6/2005 | Denk et al. |
| 2005/0151866 A1 | 7/2005 | Ando et al. |
| 2005/0200291 A1 | 9/2005 | Naugler, Jr. et al. |
| 2005/0234302 A1 | 10/2005 | MacKinnon et al. |
| 2005/0237384 A1 | 10/2005 | Jess et al. |
| 2005/0261552 A1 | 11/2005 | Muri et al. |
| 2005/0288546 A1 | 12/2005 | Sonnenschein et al. |
| 2006/0069314 A1 | 3/2006 | Farr |
| 2006/0087841 A1 | 4/2006 | Chern et al. |
| 2006/0197664 A1 | 9/2006 | Zhang et al. |
| 2006/0202036 A1 | 9/2006 | Wang et al. |
| 2006/0221250 A1 | 10/2006 | Rossbach et al. |
| 2006/0226231 A1 | 10/2006 | Johnston et al. |
| 2006/0264734 A1 | 11/2006 | Kimoto et al. |
| 2006/0274335 A1 | 12/2006 | Wittenstein |
| 2007/0010712 A1 | 1/2007 | Negishi |
| 2007/0029629 A1* | 2/2007 | Yazdi .................. B81C 1/00253 |
| | | 257/414 |
| 2007/0041448 A1 | 2/2007 | Miller et al. |
| 2007/0083085 A1 | 4/2007 | Bimkrant et al. |
| 2007/0129601 A1 | 6/2007 | Johnston et al. |
| 2007/0147033 A1 | 6/2007 | Ogawa et al. |
| 2007/0182723 A1 | 8/2007 | Imai et al. |
| 2007/0244364 A1 | 10/2007 | Luanava et al. |
| 2007/0244365 A1 | 10/2007 | Wiklof |
| 2007/0276187 A1 | 11/2007 | Wiklof et al. |
| 2007/0279486 A1 | 12/2007 | Bayer et al. |
| 2007/0285526 A1 | 12/2007 | Mann et al. |
| 2007/0293720 A1 | 12/2007 | Bayer |
| 2008/0045800 A2 | 2/2008 | Farr |
| 2008/0049132 A1 | 2/2008 | Suzuki |
| 2008/0088719 A1 | 4/2008 | Jacob et al. |
| 2008/0107333 A1 | 5/2008 | Mazinani et al. |
| 2008/0136953 A1 | 6/2008 | Barnea et al. |
| 2008/0158348 A1 | 7/2008 | Karpen et al. |
| 2008/0164550 A1* | 7/2008 | Chen ................ H01L 27/14618 |
| | | 257/432 |
| 2008/0165360 A1 | 7/2008 | Johnston |
| 2008/0192131 A1 | 8/2008 | Kim et al. |
| 2008/0218598 A1 | 9/2008 | Harada et al. |
| 2008/0218615 A1 | 9/2008 | Huang et al. |
| 2008/0218824 A1 | 9/2008 | Johnston et al. |
| 2008/0249369 A1 | 10/2008 | Seibel et al. |
| 2009/0012361 A1 | 1/2009 | MacKinnon et al. |
| 2009/0012368 A1 | 1/2009 | Banik |
| 2009/0021588 A1 | 1/2009 | Border et al. |
| 2009/0024000 A1 | 1/2009 | Chen |
| 2009/0028465 A1 | 1/2009 | Pan |
| 2009/0074265 A1 | 3/2009 | Huang et al. |
| 2009/0091645 A1 | 4/2009 | Trimeche et al. |
| 2009/0137893 A1 | 5/2009 | Seibel et al. |
| 2009/0147077 A1 | 6/2009 | Tani et al. |
| 2009/0154886 A1 | 6/2009 | Lewis et al. |
| 2009/0160976 A1 | 6/2009 | Chen et al. |
| 2009/0189530 A1 | 7/2009 | Ashdown et al. |
| 2009/0208143 A1 | 8/2009 | Yoon et al. |
| 2009/0227847 A1 | 9/2009 | Tepper et al. |
| 2009/0232213 A1 | 9/2009 | Jia |
| 2009/0259102 A1 | 10/2009 | Koninckx et al. |
| 2009/0268063 A1 | 10/2009 | Ellis-Monaghan et al. |
| 2009/0292168 A1 | 11/2009 | Farr |
| 2009/0316116 A1 | 12/2009 | Melville et al. |
| 2009/0322912 A1 | 12/2009 | Blanquart |
| 2010/0026722 A1 | 2/2010 | Kondo |
| 2010/0049180 A1 | 2/2010 | Wells et al. |
| 2010/0069713 A1 | 3/2010 | Endo et al. |

(56) References Cited

U.S. PATENT DOCUMENTS

| | | |
|---|---|---|
| 2010/0102199 A1 | 4/2010 | Negley et al. |
| 2010/0121142 A1 | 5/2010 | OuYang et al. |
| 2010/0121143 A1 | 5/2010 | Sugimoto et al. |
| 2010/0123775 A1 | 5/2010 | Shibasaki |
| 2010/0134608 A1 | 6/2010 | Shibasaki |
| 2010/0134662 A1 | 6/2010 | Bub |
| 2010/0135398 A1 | 6/2010 | Wittmann et al. |
| 2010/0137684 A1 | 6/2010 | Shibasaki et al. |
| 2010/0149421 A1 | 6/2010 | Lin et al. |
| 2010/0157037 A1 | 6/2010 | Iketani et al. |
| 2010/0157039 A1 | 6/2010 | Sugai |
| 2010/0165087 A1 | 7/2010 | Corso et al. |
| 2010/0171429 A1 | 7/2010 | Garcia et al. |
| 2010/0182446 A1 | 7/2010 | Matsubayashi |
| 2010/0198009 A1 | 8/2010 | Farr et al. |
| 2010/0198134 A1 | 8/2010 | Eckhouse et al. |
| 2010/0201797 A1 | 8/2010 | Shizukuishi et al. |
| 2010/0228089 A1 | 9/2010 | Hoffman et al. |
| 2010/0261961 A1 | 10/2010 | Scott et al. |
| 2010/0274082 A1 | 10/2010 | Iguchi et al. |
| 2010/0274090 A1 | 10/2010 | Ozaki et al. |
| 2010/0305406 A1 | 12/2010 | Braun et al. |
| 2010/0309333 A1 | 12/2010 | Smith et al. |
| 2011/0028790 A1 | 2/2011 | Farr et al. |
| 2011/0034769 A1 | 2/2011 | Adair et al. |
| 2011/0051390 A1* | 3/2011 | Lin .................. H01L 27/14618 361/818 |
| 2011/0063483 A1 | 3/2011 | Rossi et al. |
| 2011/0122301 A1 | 5/2011 | Yamura et al. |
| 2011/0149358 A1 | 6/2011 | Cheng |
| 2011/0181709 A1 | 7/2011 | Wright et al. |
| 2011/0181840 A1 | 7/2011 | Cobb |
| 2011/0184239 A1 | 7/2011 | Wright et al. |
| 2011/0184243 A1 | 7/2011 | Wright et al. |
| 2011/0208004 A1 | 8/2011 | Feingold et al. |
| 2011/0212649 A1 | 9/2011 | Stokoe et al. |
| 2011/0237882 A1 | 9/2011 | Saito |
| 2011/0237884 A1 | 9/2011 | Saito |
| 2011/0245605 A1 | 10/2011 | Jacobsen et al. |
| 2011/0245616 A1 | 10/2011 | Kobayashi |
| 2011/0255844 A1 | 10/2011 | Wu et al. |
| 2011/0274175 A1 | 11/2011 | Sumitomo |
| 2011/0279679 A1 | 11/2011 | Samuel et al. |
| 2011/0288374 A1 | 11/2011 | Hadani et al. |
| 2011/0292258 A1 | 12/2011 | Adler et al. |
| 2011/0295061 A1 | 12/2011 | Haramaty et al. |
| 2012/0004508 A1 | 1/2012 | McDowall et al. |
| 2012/0014563 A1 | 1/2012 | Bendall |
| 2012/0029279 A1 | 2/2012 | Kucklick |
| 2012/0033118 A1 | 2/2012 | Lee et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0078052 A1 | 3/2012 | Cheng |
| 2012/0098933 A1 | 4/2012 | Robinson et al. |
| 2012/0104230 A1 | 5/2012 | Eismann et al. |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0155761 A1 | 6/2012 | Matsuoka |
| 2012/0157774 A1 | 6/2012 | Kaku |
| 2012/0194686 A1 | 8/2012 | Lin et al. |
| 2012/0197080 A1 | 8/2012 | Murayama |
| 2012/0200685 A1 | 8/2012 | Kawasaki et al. |
| 2012/0242975 A1 | 9/2012 | Min et al. |
| 2012/0262621 A1 | 10/2012 | Sato et al. |
| 2012/0281111 A1 | 11/2012 | Jo et al. |
| 2012/0327270 A1 | 12/2012 | Shirakawa et al. |
| 2013/0018256 A1 | 1/2013 | Kislev et al. |
| 2013/0035545 A1 | 2/2013 | Ono |
| 2013/0053642 A1 | 2/2013 | Mizuyoshi et al. |
| 2013/0070071 A1 | 3/2013 | Peltie et al. |
| 2013/0126708 A1 | 5/2013 | Blanquart |
| 2013/0127934 A1 | 5/2013 | Chiang |
| 2013/0135589 A1 | 5/2013 | Curtis et al. |
| 2013/0144120 A1 | 6/2013 | Yamazaki |
| 2013/0155215 A1 | 6/2013 | Shimada et al. |
| 2013/0155305 A1 | 6/2013 | Shintani |
| 2013/0158346 A1 | 6/2013 | Soper et al. |
| 2013/0184524 A1 | 7/2013 | Shimada et al. |
| 2013/0211217 A1 | 8/2013 | Yamaguchi et al. |
| 2013/0242069 A1 | 9/2013 | Kobayashi |
| 2013/0244453 A1 | 9/2013 | Sakamoto |
| 2013/0274597 A1 | 10/2013 | Byrne et al. |
| 2013/0292571 A1 | 11/2013 | Mukherjee et al. |
| 2013/0296652 A1 | 11/2013 | Farr |
| 2013/0308837 A1 | 11/2013 | DiCarlo et al. |
| 2013/0342690 A1 | 12/2013 | Williams et al. |
| 2014/0005532 A1 | 1/2014 | Choi et al. |
| 2014/0022365 A1 | 1/2014 | Yoshino |
| 2014/0031623 A1 | 1/2014 | Kagaya |
| 2014/0052004 A1 | 2/2014 | D'Alfonso et al. |
| 2014/0073852 A1 | 3/2014 | Banik et al. |
| 2014/0073853 A1 | 3/2014 | Swisher et al. |
| 2014/0078278 A1 | 3/2014 | Lei |
| 2014/0088363 A1 | 3/2014 | Sakai et al. |
| 2014/0104466 A1 | 4/2014 | Fossum |
| 2014/0110485 A1* | 4/2014 | Toa .................. G06K 7/10821 235/462.21 |
| 2014/0160318 A1 | 6/2014 | Blanquart et al. |
| 2014/0163319 A1 | 6/2014 | Blanquart et al. |
| 2014/0198249 A1 | 7/2014 | Tanaka et al. |
| 2014/0203084 A1 | 7/2014 | Wang |
| 2014/0225215 A1* | 8/2014 | Chien .................. H01L 24/05 257/447 |
| 2014/0267655 A1 | 9/2014 | Richardson et al. |
| 2014/0267851 A1 | 9/2014 | Rhoads |
| 2014/0268860 A1 | 9/2014 | Talbert et al. |
| 2014/0275764 A1 | 9/2014 | Shen et al. |
| 2014/0288365 A1 | 9/2014 | Henley et al. |
| 2014/0300698 A1 | 10/2014 | Wany |
| 2014/0316199 A1 | 10/2014 | Kucklick |
| 2014/0354788 A1 | 12/2014 | Yano |
| 2014/0364689 A1* | 12/2014 | Adair ................ H04N 5/3765 600/109 |
| 2015/0237245 A1* | 8/2015 | Renard ............... H04N 5/2254 348/222.1 |
| 2016/0183775 A1 | 6/2016 | Blanquart et al. |
| 2017/0085853 A1 | 3/2017 | Blanquart et al. |
| 2017/0230574 A1 | 8/2017 | Richardson et al. |

FOREIGN PATENT DOCUMENTS

| | | |
|---|---|---|
| CN | 201239130 A | 5/2009 |
| CN | 101449575 A | 6/2009 |
| CN | 101634749 A | 1/2010 |
| CN | 101755448 A | 6/2010 |
| CN | 102469932 A | 5/2012 |
| CN | 103185960 A | 7/2013 |
| EP | 0660616 A2 | 6/1995 |
| EP | 0904725 A1 | 3/1999 |
| EP | 1079255 A2 | 2/2001 |
| EP | 1637062 A1 | 3/2006 |
| EP | 1712177 A1 | 10/2006 |
| EP | 1819151 A1 | 8/2007 |
| EP | 2359739 A1 | 8/2011 |
| EP | 2371268 A1 | 10/2011 |
| JP | 2001-308531 A | 11/2001 |
| JP | 2002-020816 A | 1/2002 |
| JP | 2007-029746 A | 2/2007 |
| JP | 2007-240931 A | 9/2007 |
| JP | 2009-537283 A | 10/2009 |
| JP | 2010-068992 A | 4/2010 |
| JP | 2010-125284 A | 6/2010 |
| JP | 2011-055327 A | 3/2011 |
| JP | 2012-000160 A | 1/2012 |
| MX | 346174 | 3/2017 |
| WO | 9605693 | 2/1996 |
| WO | WO2009120228 A1 | 10/2009 |
| WO | 2012043771 A1 | 4/2012 |

\* cited by examiner

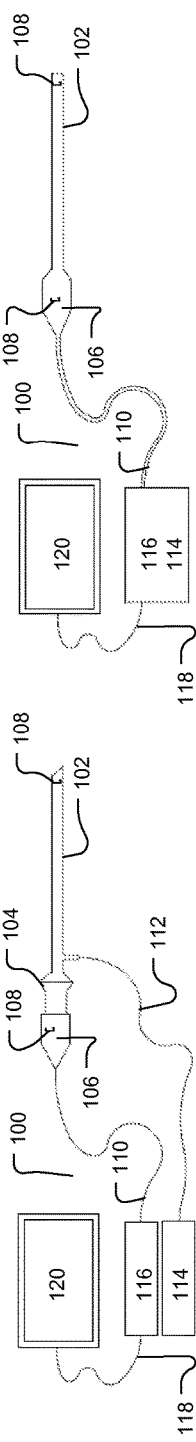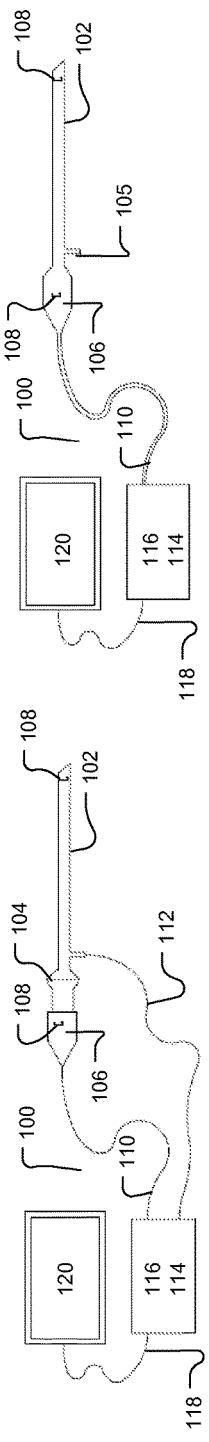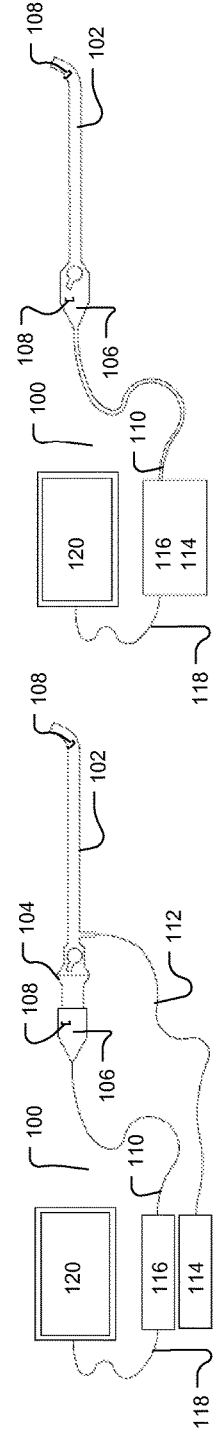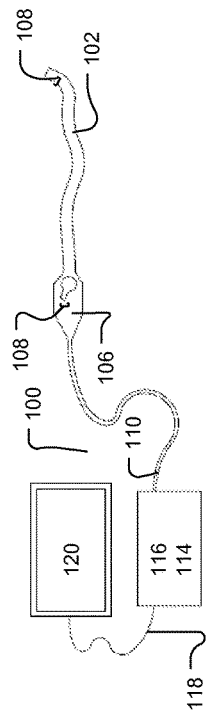

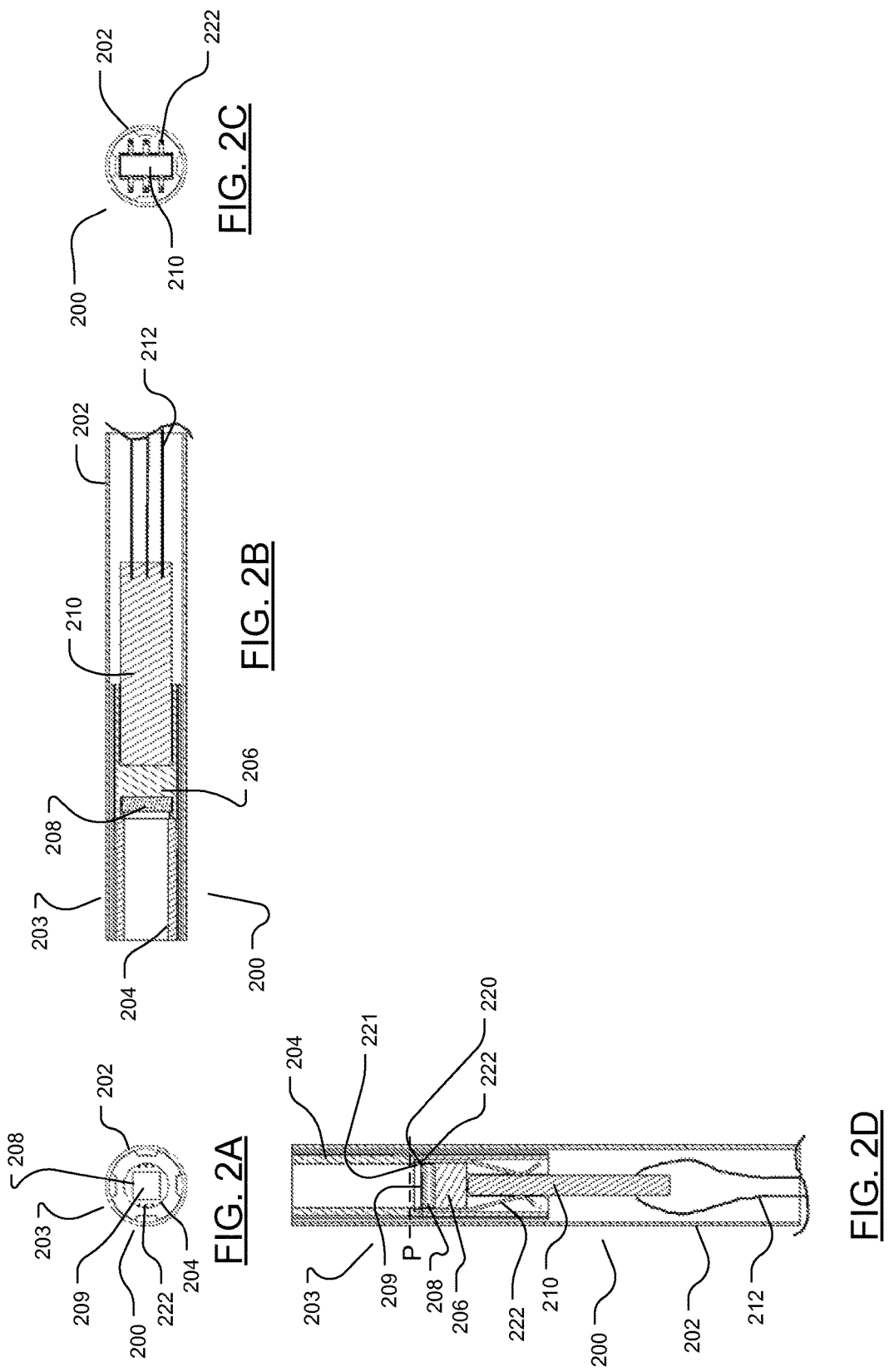

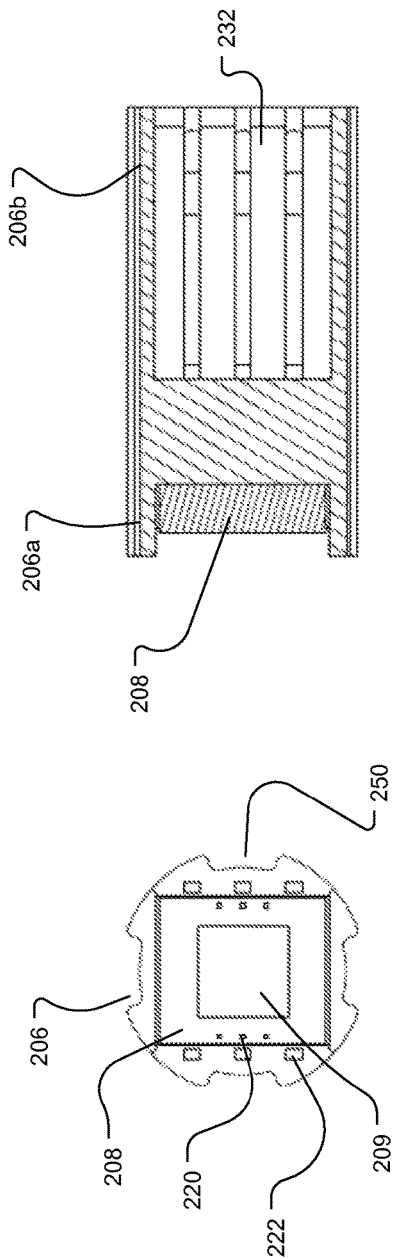
FIG. 4B
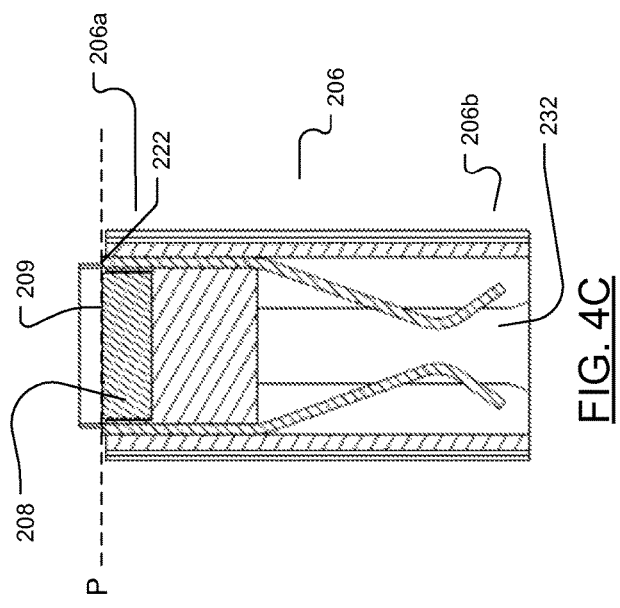
FIG. 4A
FIG. 4C

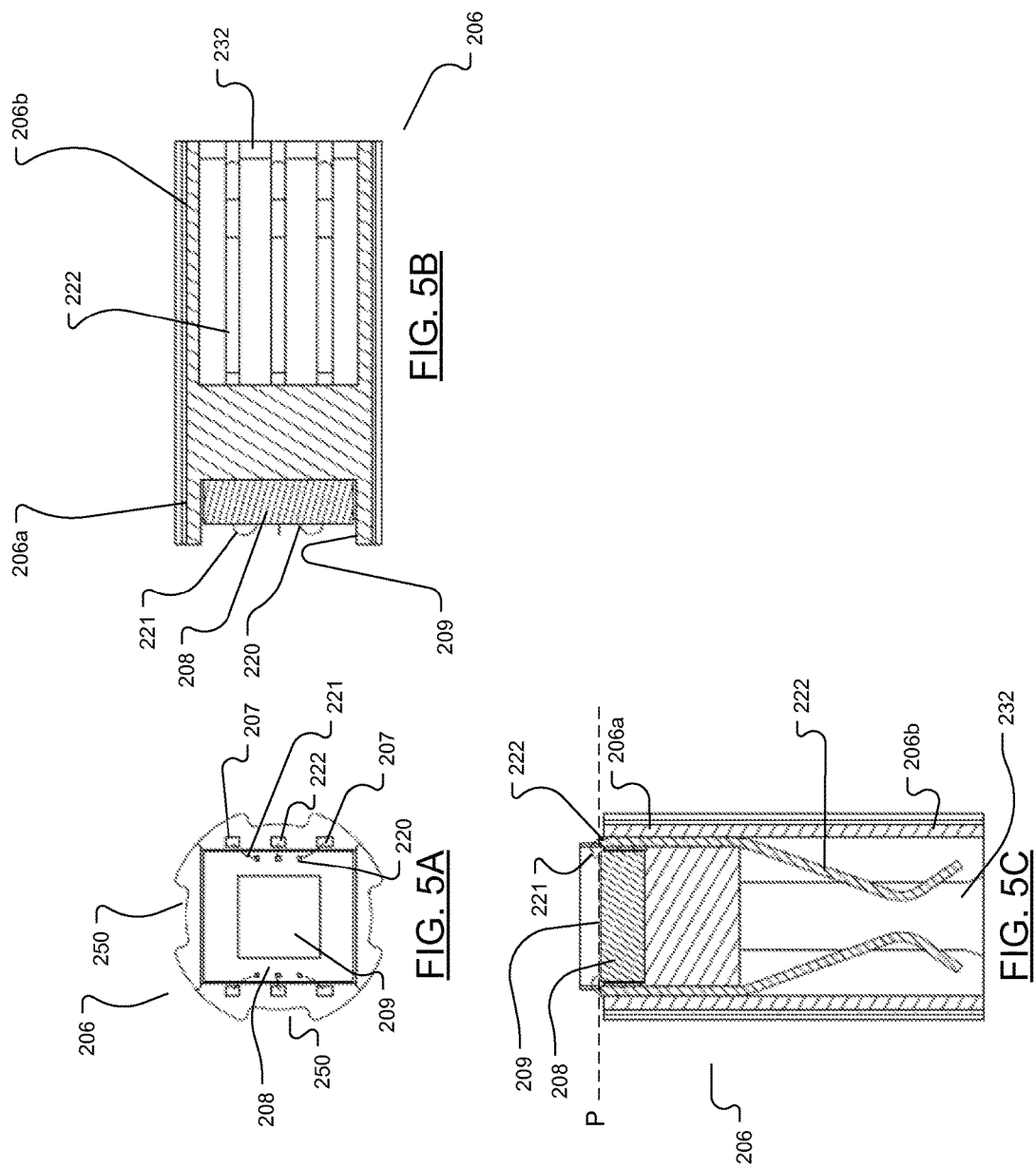

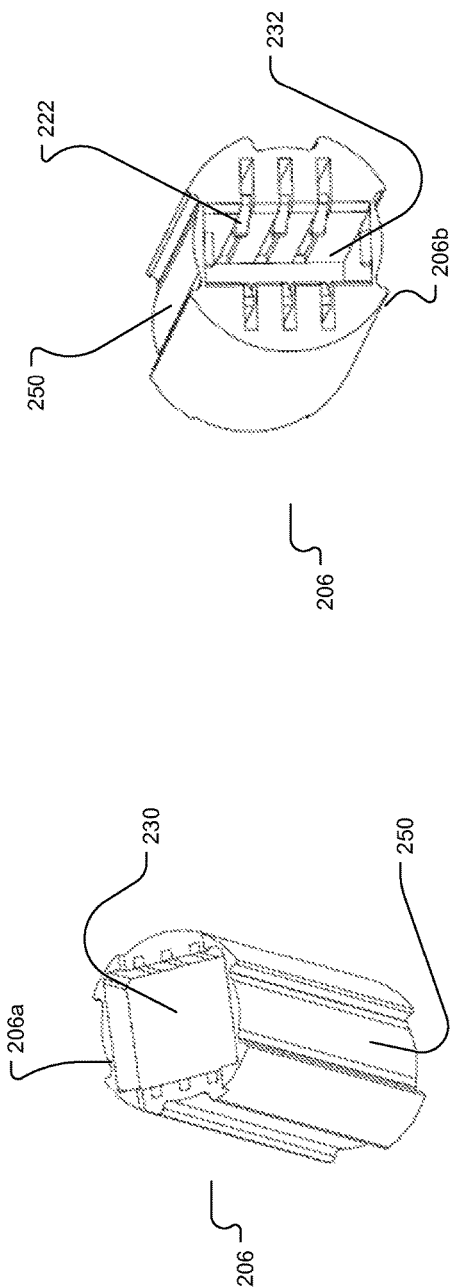
FIG. 6A
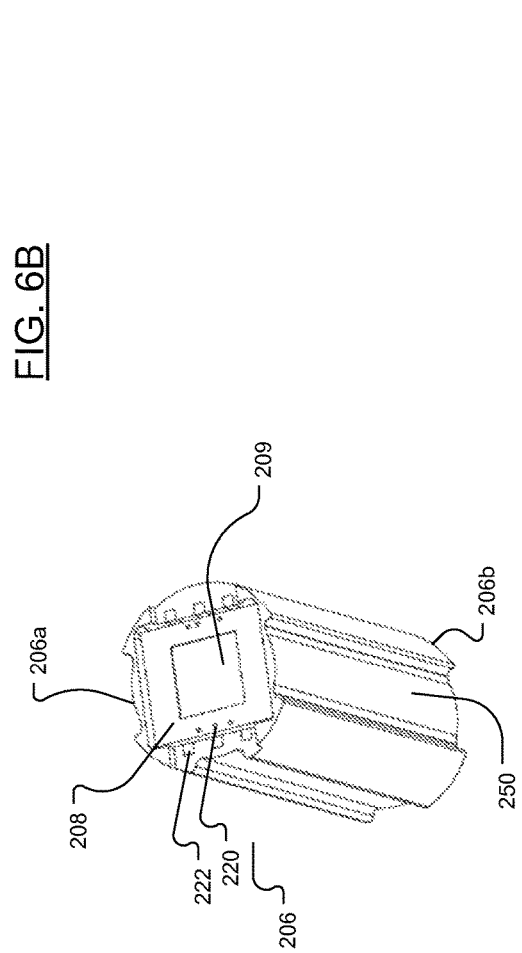
FIG. 6B
FIG. 6C

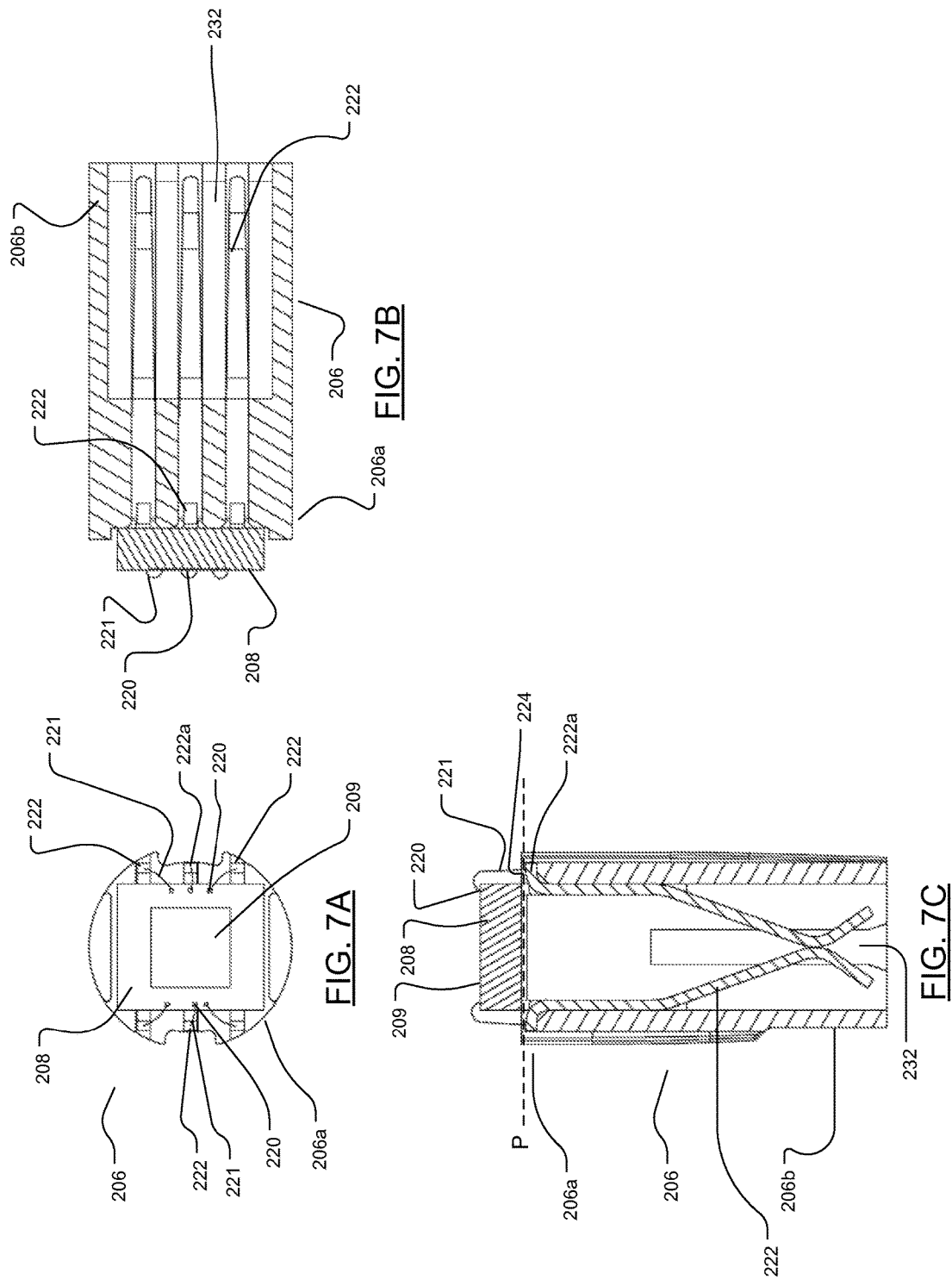

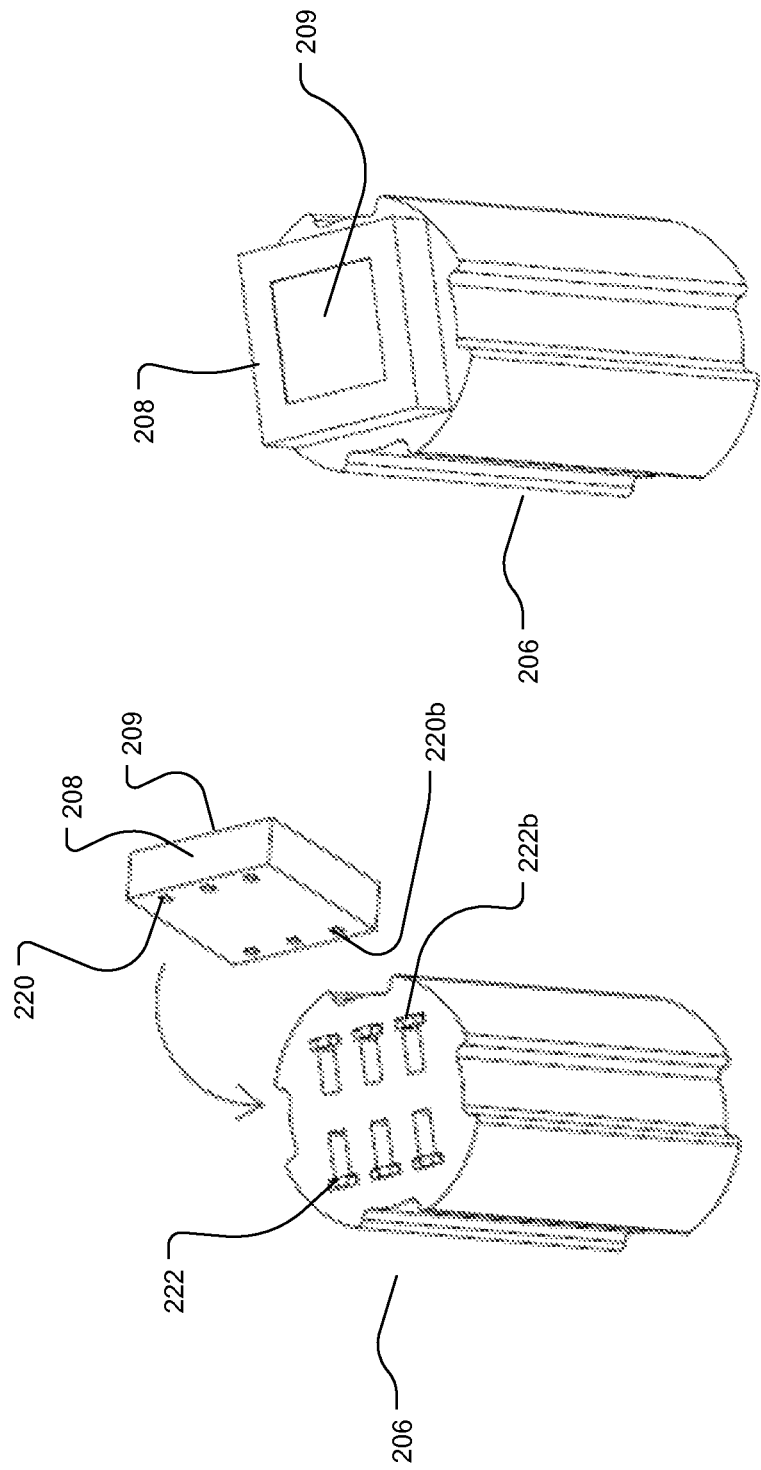

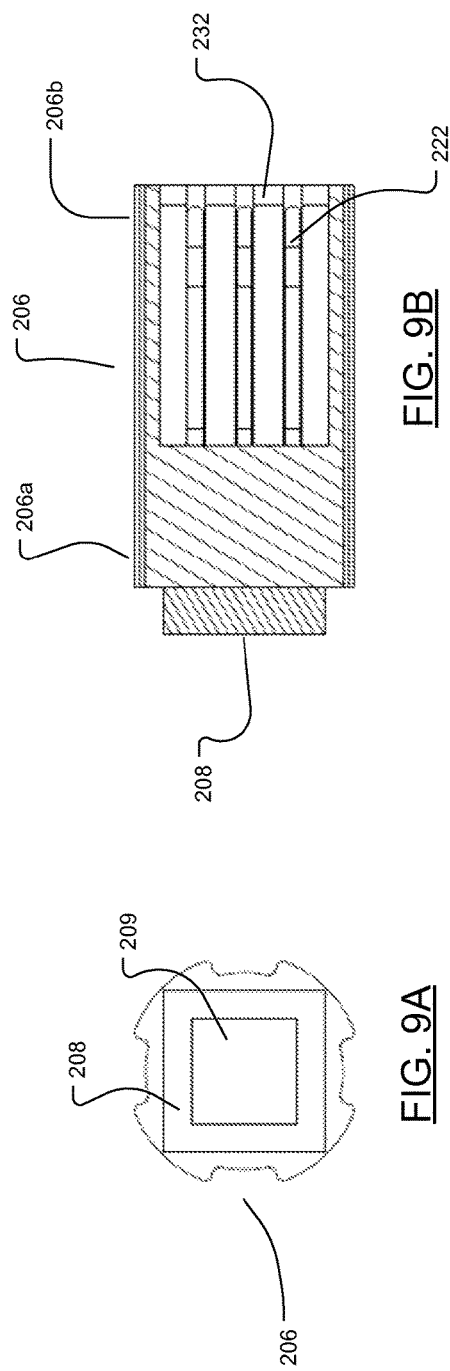

CARD EDGE CONNECTOR FOR AN IMAGING SENSOR

CROSS-REFERENCE TO RELATED APPLICATIONS

This application claims the benefit of U.S. Provisional Application No. 61/968,959, filed Mar. 21, 2014, which is hereby incorporated by reference herein in its entirety, including but not limited to those portions that specifically appear hereinafter, the incorporation by reference being made with the following exception: In the event that any portion of the above-referenced provisional application is inconsistent with this application, this application supersedes said above-referenced provisional application.

STATEMENT REGARDING FEDERALLY SPONSORED RESEARCH OR DEVELOPMENT

Not Applicable.

BACKGROUND

The disclosure relates generally to card edge connectors and more specifically, but not entirely, to card edge connectors for sensors, such as an image sensor. Advances in technology have provided advances in imaging capabilities for medical use. One area that has enjoyed some of the most beneficial advances is that of endoscopic surgical procedures because of the advances in the components that make up an endoscope.

Conventional, digital video systems used for laparoscopy, arthroscopy, ENT, gynecology and urology are based upon conventional, rigid endoscopes, which are optically and mechanically coupled to a separate hand-piece unit, which contains one or more image sensor(s). Image information is optically transmitted along the length of the endoscope, after which it is focused upon the sensor via an optical coupler.

However, due to advances in technology sensors are now being located in the distal end or distal tip of medical or other type of scopes. With such advancements come difficulties and problems associated with mechanically and electrically connecting the sensor to a printed circuit board (PCB) in such scopes. Accordingly, devices, systems and methods for connecting sensors to PCBs in the distal end or tip of a scope are needed. As will be seen, the disclosure provides such devices, systems and methods for connecting sensors to PCBs in the distal end or tip of a scope in an effective and elegant manner.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIGS. 1A-1G illustrate various embodiments of an endoscopic system in accordance with the principles and teachings of the disclosure;

FIGS. 2A-2D illustrate front, side cross-sectional, rear, and bottom cross-sectional views, respectively, of an endoscopic device in accordance with the principles and teachings of the disclosure;

FIGS. 4A-4C illustrate front, side cross-sectional and bottom cross-sectional views, respectively, of a card edge connector device with a sensor loaded therein in accordance with the principles and teachings of the disclosure;

FIGS. 5A-5C illustrate front, side cross-sectional, and bottom cross-sectional views, respectively, of a card edge connector device with a sensor loaded therein with wire bonds connecting the sensor to electrical connectors, such as pins or pads, of the connector in accordance with the principles and teachings of the disclosure;

FIGS. 6A-6C illustrate a front perspective view of a card edge connector device, a rear perspective view of the card edge connector device, and a front perspective view of the card edge connector device with a sensor loaded therein, respectively, in accordance with the principles and teachings of the disclosure;

FIGS. 7A-7C illustrate front, side cross-sectional and bottom cross-sectional views, respectively, of a card edge connector device with a sensor loaded proud of a plane of the connector in accordance with the principles and teachings of the disclosure;

FIGS. 8A-8B illustrate perspective views of a card edge connector device for use with a backside illuminated sensor loaded proud of a plane of the connector in accordance with the principles and teachings of the disclosure;

FIGS. 9A-9C illustrate front, side cross-sectional and bottom cross-sectional views, respectively, of a card edge connector device with a sensor loaded proud of a plane of the connector in accordance with the principles and teachings of the disclosure.

DETAILED DESCRIPTION

Figure 3C:
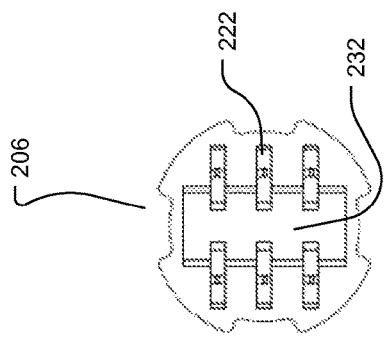
FIGS. 3A-3D illustrate front, side cross-sectional, rear, and bottom cross-sectional views, respectively, of a card edge connector device in accordance with the principles and teachings of the disclosure.
Figure 3B:
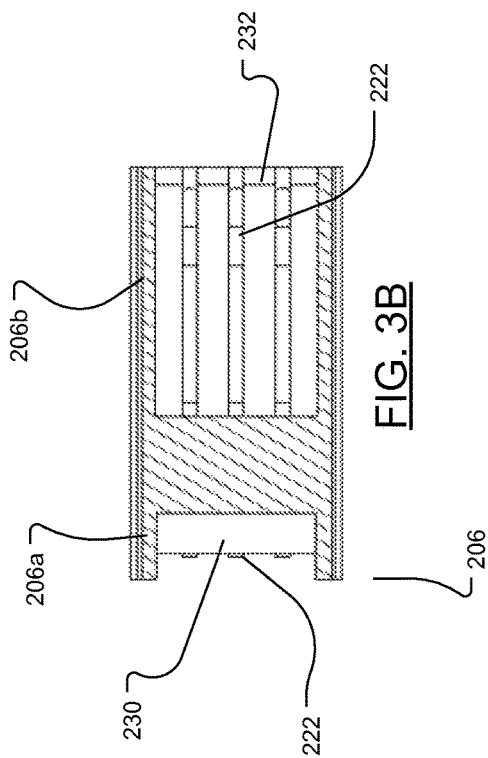
Figure 3A:
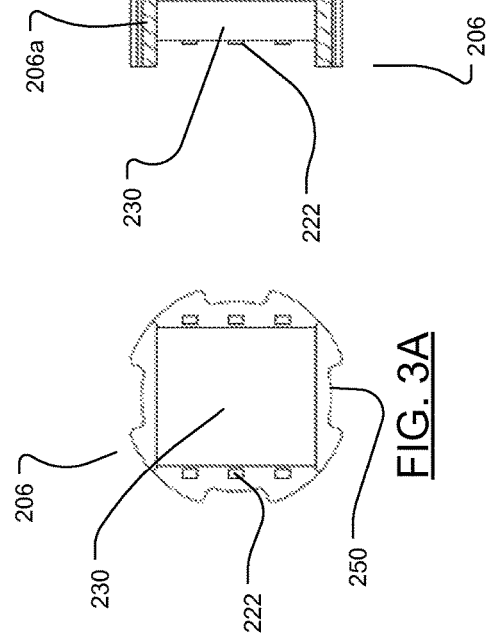
Figure 3D:
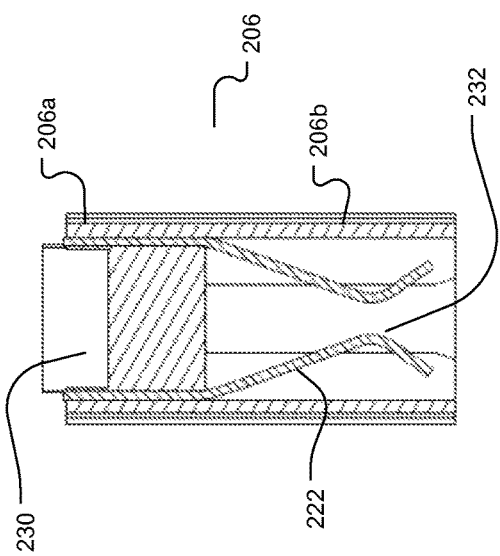

The disclosure extends to devices, systems and methods for connecting one or more sensors to one or more printed circuit boards (PCB) in the distal end or tip of a scope where lateral space may be limited. The disclosure also extends to a card edge connector for an image sensor for protecting the sensor and conveying information from the sensor to the PCB, wherein the image sensor may be connected at one end of the card edge connector and the PCB may be connected at the opposite end of the card edge connector. The disclosure also extends to a card edge connector for an image sensor for protecting the sensor and conveying information from the sensor to the PCB, wherein the image sensor may be connected at one end of the card edge connector and the PCB may be connected at the opposite end of the card edge connector in a vertical and substantially perpendicular orientation with respect to the printed circuit board. A portion of a PCB may comprise traces leading to the edge of the board that are intended to plug into a matching card edge connector socket. The card edge connector may only require a female connector where the male connector may be formed out of the edge of the PCB.

In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

Referring now to FIG. 1, there is illustrated various embodiments of an endoscopic system 100. It will be appreciated that the system 100 may comprise many different configurations. One example is shown in FIG. 1A, which illustrates an endoscopic system 100 comprising a rigid angled scope 102, an optical coupler 104, a handpiece 106, an image sensor 108, which may be located within the handpiece 106 or distally at a tip of the endoscope 102 as illustrated in dashed lines, an electronic cable 110, a light cable 112, such as a fiber optic cable, a light source 114, a control unit 116, such as a camera control unit (CCU), a video cable 118 and a display 120.

The system configuration shown in FIG. 1B illustrates an endoscopic system 100 comprising a rigid angled scope 102, an optical coupler 104, a handpiece 106, an image sensor 108, which may be located within the handpiece 106 or distally at a tip of the endoscope 102 as illustrated in dashed lines, an electronic cable 110, a light cable 112, such as a fiber optic cable, a control unit 116, such as a camera control unit (CCU), with an integrated light source 114, a video cable 118, and a display 120.

The system configuration shown in FIG. 1C illustrates an endoscopic system 100 comprising an articulating scope 102, an optical coupler 104, a handpiece 106, an image sensor 108, which may be located within the handpiece 106 or distally at a tip of the endoscope 102 as illustrated in dashed lines, an electronic cable 110, a light cable 112, such as a fiber optic cable, a light source 114, a control unit 116, such as a camera control unit (CCU), a video cable 118 and a display 120.

The system configuration shown in FIG. 1D illustrates an endoscopic system 100 comprising a handpiece 106 with an integrated rigid 0 degree scope 102, an image sensor 108, which may be located within the handpiece 106 or distally at a tip of the scope 102 as illustrated in dashed lines, a combined electronic and light cable 110, a control unit 116, such as a camera control unit (CCU) with an integrated light source 114, a video cable 118 and a display 120.

The system configuration shown in FIG. 1E illustrates an endoscopic system 100 comprising a handpiece 106 with an integrated rigid angled scope 102 and rotation post 105, an image sensor 108, which may be located within the handpiece 106 or distally at a tip of the scope 102 as illustrated in dashed lines, a combined electronic and light cable 110, a control unit 116, such as a camera control unit (CCU) with an integrated light source 114, a video cable 118 and a display 120.

The system configuration shown in FIG. 1F illustrates an endoscopic system 100 comprising a handpiece 106 with an integrated articulating scope 102, an image sensor 108, which may be located within the handpiece 106 or distally at a tip of the scope 102 as illustrated in dashed lines, a combined electronic and light cable 110, a control unit 116, such as a camera control unit (CCU) with an integrated light source 114, a video cable 118 and a display 120.

The system configuration shown in FIG. 1G illustrates an endoscopic system 100 comprising a handpiece 106 with an integrated flexible scope 102, an image sensor 108, which may be located within the handpiece 106 or distally at a tip of the scope 102 as illustrated in dashed lines, a combined electronic and light cable 110, a control unit 116, such as a camera control unit (CCU) with an integrated light source 114, a video cable 118 and a display 120.

It will be appreciated that any of the above-identified configurations for an endoscopic system shown in FIGS. 1A-1G, any combination of the above elements in a different configuration, and any other configuration used for Minimally Invasive Surgery, are intended to fall within the scope of this disclosure.

In an implementation of the system 100 for providing an image in a light deficient environment, the system may comprise a surgical scope, which itself may comprise a tubular member having a proximal portion and a distal portion. The system 100 may further comprise a light source, a camera control unit (CCU), and a display. As described more fully herein below, the surgical scope may comprise a connector assembly that may be located at the distal portion of the tubular member and may have a first end, a second end, and a plurality of electrical connectors. The connector assembly may also receive therein a printed circuit board and an image sensor. In such an implementation, the image sensor may be connected to the connector assembly at the first end of and the printed circuit board may be connected to the connector assembly at the second end, such that the connector assembly attaches the image sensor at the distal portion of the tubular member and electrically connects the image sensor to the printed circuit board via the plurality of electrical connectors, thereby providing electrical communication between the image sensor and the printed circuit board.

Referring now to FIGS. 2A-2D, an endoscopic device 200 is illustrated. The endoscopic device 200 may comprise a tubular member, such as an outer scope tube 202, a lens assembly 204, a connector or card edge connector 206, an image sensor 208, a card edge PCBA 210, and a plurality of wires and/or a wire harness and/or other communication components 212. It will be appreciated that the connector 206 may sometimes be referred to herein as a connector assembly 206 because a connector may comprise subcomponents that when assembled form a complete connector.

The endoscopic device is illustrated in FIGS. 2A-2D with the imaging sensor 208 located at a distal portion 203, or at a tip, of the outer scope tube 202. It will be appreciated that the endoscopic device 200 may comprise: an outer scope tube 202, a lens assembly 204 complete with various optical elements that may be used in conventional endoscopic devices, which are not shown for purposes of clarity, a card edge connector 206 for housing or securing an image sensor 208 at a first end, which may be a distal end or distal portion 206a of the connector 206 as illustrated, connecting to a card edge PCBA 210 at a second or proximal end 206b, and wires and/or a wire harness and/or other communication components 212 to convey a signal from the card edge PCBA 210 to the image processor (not illustrated), which may be located remotely with respect to the image sensor, for example, in the handpiece of an imaging device or camera, or in the camera control unit (CCU), or further up the length of a lumen.

The image sensor 208 may include an image sensor silicon die, a pixel array 209, and a plurality of sensor pads for electrically communicating with corresponding electrical connectors, such as pins or pads. The image sensor 208 may include a plurality of bonds 221, such as wire bonds, which connect the plurality of sensor pads 220 to a corresponding plurality of electrical connectors 222, such as pins or pads, which may be part of the connector 206.

It will be appreciated that the card edge connector 206 may be used as a package to house the sensor 208. Additionally, it should be understood that structures of the card edge connector 206 may aid in the manufacture and transport of the sensor as part of sensor packaging. One purpose for the card edge connector or package 206 is to simplify the process of connecting the imaging sensor 208 to the wiring harness 212. The card edge connector or package 206 may facilitate sensor connection to a wiring harness 212.

It will be appreciated that FIGS. 2A-2D illustrate the PCBA 210 being connected to the connector assembly 206 at the second end 206b of the connector assembly 206. Conversely, the image sensor 208 is illustrated as being connected to the connector assembly 206 at the first end 206a, such that the connector assembly 206 attaches the image sensor 208 at the distal portion 203 of the tubular member 202 and electrically connects the image sensor 208 to the PCBA 210 via the plurality of electrical connectors 222, thereby providing electrical communication between the image sensor 208 and the PCBA 210. It will be appreciated by those skilled in the art that the connector assembly 206 may be used in conjunction with any elongated configuration in addition to a generally tubular configuration and such elongated configurations are intended to fall within the scope of this disclosure.

The connector assembly 206 may operate to attach the image sensor 208 within the distal portion 203 of the tubular member 202 in a vertical and substantially perpendicular orientation (as illustrated best in FIG. 2D) with respect to the PCBA 210. In an implementation, the PCBA 210 may be attached perpendicularly out of the center of and with respect to the image sensor 208. In an implementation, the PCBA 210 may be attached perpendicularly off of an edge of and with respect to the image sensor 208. As illustrated, the image sensor 208 may be located substantially beneath a plane (illustrated by dashed line P in FIG. 2D) of the electrical connectors 222 at the first end 206a of the connector assembly 206, such that the plane of the electrical connectors 222 at the first end 206a of the connector assembly 206 is located substantially above the image sensor 208. In this configuration, the pixel array 209 of the image sensor 208 is located beneath the plane (illustrated by dashed line P in FIG. 2D) of the electrical connectors 222 at the first end 206a of the connector assembly 206.

Referring now to FIGS. 3A-3D, the figures illustrate a front, side cross-sectional, rear, and bottom cross-sectional views, respectively, of the card edge connector device 206 in accordance with the principles and teachings of the disclosure. The card edge connector 206 of FIGS. 3A-3D is illustrated without the scope or endoscopic device, including the outer scope tube 202, for purposes of clarity and simplicity in discussing the details of the connector 206.

It will be appreciated that the card edge connector 206 may be configured, dimensioned and built to help minimize the overall size of the package, for example, in the x-dimension (width) and the y-dimension (height). Accordingly, one end 206a of the connector 206, which may be a first end or at the distal end or distal portion, may be optimized for placement of the sensor 208 in order to protect the wirebonds that may connect the sensor 208 to the plurality of electrical connectors 222, such as pins or pads, of the connector 206, and to provide overall protection of the sensor 208.

To facilitate the above, the card edge connector 206 may comprise a cavity or recess 230 for receiving therein the sensor 208 and silicon die. The other end 206b, which may be a second end or a proximal end, of the connector 206 may be optimized to accept the edge card PCBA 210 (illustrated best in FIGS. 2B and 2D). At this end 206b, a first slot, socket or receptacle 232 (as illustrated best in FIGS. 3B-3D) may be provided to accept or receive therein the edge card PCBA 210. It will be appreciated that the PCBA 210 may be held in the first slot, socket or receptacle 232 via a bias force. The plurality of electrical connectors 222 may extend into the first slot, socket or receptacle 232, such that when the PCBA 210 is located within the first slot 232 the electrical connectors 222 of the connector assembly 206 may be in electrical communication with corresponding electrical connectors on the PCBA 210. The connector 206 may further comprise a vertical slot or channel 250 for receiving fiber optic cable strands therein.

FIGS. 4A-4C illustrate a front, side cross-sectional, and bottom cross-sectional views, respectively, of the card edge connector device 206 with a sensor 208 loaded therein in accordance with the principles and teachings of the disclosure. It will be appreciated that the sensor 208 may be loaded in the cavity 230 as discussed above in connection with FIGS. 3A-3D. It will be appreciated that the imaging sensor 208 and silicon die may be attached or otherwise connected to the connector 206 using any mechanical mechanism and/or an adhesive or other bond. For example, the imaging sensor 208 may comprise a plurality of sensor pads or electrical connectors 220 that may be bonded or otherwise connected to the electrical connectors 222 of the card edge connector 206 with a plurality of bonds 221, such as wire bonds.

In the configuration illustrated in FIGS. 4A-4C, the pixel array 209 of the image sensor 208 is located on the same plane or substantially the same plane (illustrated by dashed line P in FIG. 4C) as the electrical connectors 222 at the first end 206a of the connector assembly 206.

In an implementation of the disclosure illustrated best in FIGS. 7A-7C, adhesive may be used to attach the sensor 208 to the connector 206. The adhesive may be electrically conductive adhesive, and may be, for example, gold or silver filled adhesive or other metallic filled adhesive. The adhesive may be placed in controlled locations of the connector 206 to electrically connect the silicon die to a specific pin of the connector 206, such as the ground pin. As illustrated best in FIG. 7C, the controlled location may be an individual cavity or other receptacle 224 to receive the electrically conductive adhesive therein. As illustrated in 7C, a ground pin 222a is shown as being electrically connected to the sensor pad 220 by a wire bond 221 to the ground pin 222a. In other words, the ground pin 222a may be electrically connected to the silicon die of the sensor by an electrically conductive adhesive to provide an improved electrical ground path for the sensor. As illustrated, the wire bond 221 may be run on the outside of the sensor to the one or more electrical connectors 222, such as pins. It will be appreciated that the attachment of the electrically conductive adhesive to the ground pin 222a may reduce the amount of noise in the sensor 208 and may increase signal integrity as compared to a sensor attached to a ground pin without any epoxy or electrically conductive adhesive.

FIGS. 5A-5C illustrate front, side cross-sectional, and bottom cross-sectional views, respectively, of the card edge connector device 206 with a sensor 208 loaded therein with wire bonds 221 connecting the sensor 208 to electrical connectors 222, such as pins or pads, of the connector 206 in accordance with the principles and teachings of the disclosure. As illustrated best in FIG. 5B, the connector 206 may comprise the cavity 230 that may be defined by a sidewall 209. In various implementations, the sidewall 209 may comprise a height, such that the sidewall 209 extends above and beyond the sensor 208. In various implementations, the connector assembly 206 may comprise the cavity 230 or a partial cavity that may comprise a sidewall 209 and that is located at the first end 206a of the connector 206. It will be appreciated that the image sensor 208 may be located within the cavity 230 or partial cavity, such that the sidewall 209 surrounds at least a portion of the image sensor 208, thereby protecting the image sensor 208 and electrical connectors 221, 222 from damage. In an implementation, the image sensor 208 may be completely surrounded by the sidewall 209. In an implementation, the image sensor 208 may be partially surrounded by the sidewall 209. In an implementation, the image sensor 208 may not be surrounded by the sidewall 209, but may instead sit proud of and with respect to the connector 206.

In the configuration illustrated in FIGS. 5A-5C, the pixel array 209 of the image sensor 208 is located on the same plane or substantially the same plane (illustrated by dashed line P in FIG. 5C) as the electrical connectors 222 at the first end 206a of the connector assembly 206.

FIGS. 6A-6C illustrate a front, three-dimensional view of the card edge connector device 206, a rear, three-dimensional view of the card edge connector device 206, and a front, three-dimensional view of the card edge connector device 206 with a sensor 208 loaded therein, respectively, in accordance with the principles and teachings of the disclosure. The three images illustrated in FIGS. 6A-6C, illustrate the concept disclosed herein for the card edge connector 206. In an implementation, the housing of the connector 206 may comprise 3.5 mm housing outer diameter. In an implementation, the connector 206 may comprise six contacts or electrical connectors 222. In an implementation, the connector 206 may comprise a fine pitch (e.g., about 0.5 mm to about 0.6 mm). In an implementation, the connector 206 may comprise a first end or distal end 206a comprising the cavity or recess 230 to hold and receive the sensor die therein. In an implementation, the connector 206 may comprise a second end or proximal end 206b comprising a socket or receptacle 232 to accept or receive a micro edge card or PCBA therein. In an implementation, the PCBA may comprise a rigid PCB and features to connect a wire harness as is known in the art. In an implementation, the PCBA may comprise a flat flexible PCB.

FIGS. 7A-7C illustrate front, side cross-sectional and bottom cross-sectional views, respectively, of a card edge connector device 206 with a sensor 208 loaded proud of a plane of the connector in accordance with the principles and teachings of the disclosure. The figures illustrate an implementation in which the sensor 208 may sit proud above the plane (represented by dashed line P) of the electrical connectors 222, such as pins or pads, at the first end 206a of the connector assembly 206 as illustrated best in FIG. 7C. In this configuration, the pixel array 209 of the image sensor 208 is located above a plane (represented by dashed line P) of the electrical connectors 222 at the first end 206a of the connector assembly 206. This configuration may allow the electrical connectors 222, such as pins or pads, of the connector assembly 206 to sit under the sensor 208 rather than being positioned on either side of the sensor 208 as in other implementations disclosed herein. This configuration may enable a smaller overall housing diameter and an overall smaller housing package or assembly for use with tubular members having small diameters, such as an endoscope having a diameter of 5 mm or less.

In an implementation of the disclosure illustrated best in FIGS. 7A-7C, adhesive may be placed in controlled locations of the connector 206 to electrically connect the silicon die of the image sensor 208 to a specific pin of the connector 206, such as the ground pin. As illustrated best in FIG. 7C, the controlled location may be an individual cavity or other receptacle 224 to receive the electrically conductive adhesive therein. As illustrated in 7C, a ground pin 222a is shown as being electrically connected to the sensor pad 220 by a wire bond 221 to the ground pin 222a. In other words, the ground pin 222a may be electrically connected to the silicon die of the sensor by an electrically conductive adhesive to provide an improved electrical ground path for the sensor. As illustrated, the wire bond 221 may be run on the outside of the sensor to the one or more electrical connectors 222, such as pins. This configuration allows for an overall smaller housing for use with tubular members having small diameters, such as an endoscope having a diameter of 5 mm or less. It will be appreciated that the attachment of the electrically conductive adhesive to the ground pin 222a may reduce the amount of noise in the sensor 208 and may increase signal integrity as compared to a sensor attached to a ground pin without any epoxy or electrically conductive adhesive.

FIGS. 8A-8B illustrate perspective views of a card edge connector device 206 for use with a backside illuminated sensor 208 loaded proud of a plane P of the connector 206 in accordance with the principles and teachings of the disclosure. In this implementation, the pixel array 209 of the image sensor 208 is located above a plane of the electrical connectors 222 at the first end 206a of the connector assembly 206. The figures illustrate an implementation in which the sensor 208 is constructed using a backside illumination (BSI) manufacturing process resulting in the sensor pads 220 being located on the opposite side of the silicon die as the pixel array 209. As shown, this BSI sensor may be used with the card edge connector 206 disclosed herein. The pads 220 of BSI sensor 208 may be bonded directly to the electrical connectors 222, such as pins or pads, of the card edge connector 206 without the need for wire bonds. Referring specifically to FIG. 8A, pad 220b may be bonded directly to the electrical connector 222b without the need for wire bonds. Such direct bonding may occur with respect to all sensor pads 220 and all electrical connectors 222. It will be appreciated that the pads 220 that may be located on the underside of the sensor 208 may be soldered onto the electrical connectors 222 of the connector assembly 206.

FIGS. 9A-9C illustrate front, side cross-sectional and bottom cross-sectional views, respectively, of a card edge connector device 206 with a sensor 208 loaded proud of a plane (represented by dashed line P) at the first end 206a of the connector assembly 206 in accordance with the principles and teachings of the disclosure. In this implementation, the pixel array 209 of the image sensor 208 is located above a plane (represented by dashed line P) of the electrical connectors 222 at the first end 206a of the connector assembly 206.

The figures illustrate an implementation in which the sensor 208 is constructed using a backside illumination (BSI) manufacturing process resulting in the sensor pads 220 being located on the opposite side of the silicon die as the pixel array 209. As can be seen in FIGS. 9A-9C, which implement the details of FIGS. 8A-8B, this configuration may allow the card edge connector 206 diameter to shrink with respect to the size of the sensor 208 resulting in a more efficient use of the limited space available in a tubular member having a sensor located distally therein, while still retaining the benefits of the connector assembly 206. This efficiency gain can be used to put a larger sensor in a specific scope diameter, or to shrink the scope diameter around a specific sensor size, either of which may result in improved clinical efficiency.

It will be appreciated that the disclosure illustrates in FIGS. 1A-6C and describes herein novel devices, systems and methods for packaging a silicon imaging sensor die that: (1) protects the sensor 208 and wire bonds 221 from damage; and/or (2) minimizes the footprint of the final card edge connector 206 assembly; and/or (3) enables simple mechanical connection to a PCBA with an attached wire harness that carries data to a remote or off-site image processing hardware. The above characteristics may be important for applications in which space is minimal, such as in an endoscopic application with the image sensor located distally within a tip of the scope or any other application in which physical space is limited.

Figure 10B:
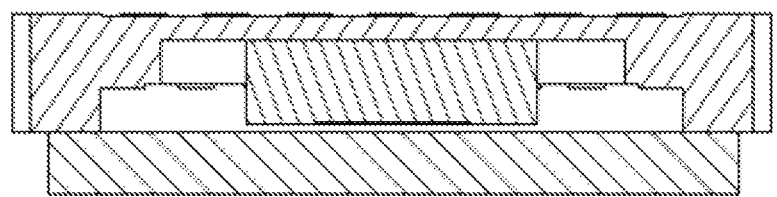
FIGS. 10A and 10B illustrate a front view and a side cross-sectional view, respectively, of a conventional, prior art packaged imaging sensor device.
Figure 10A:
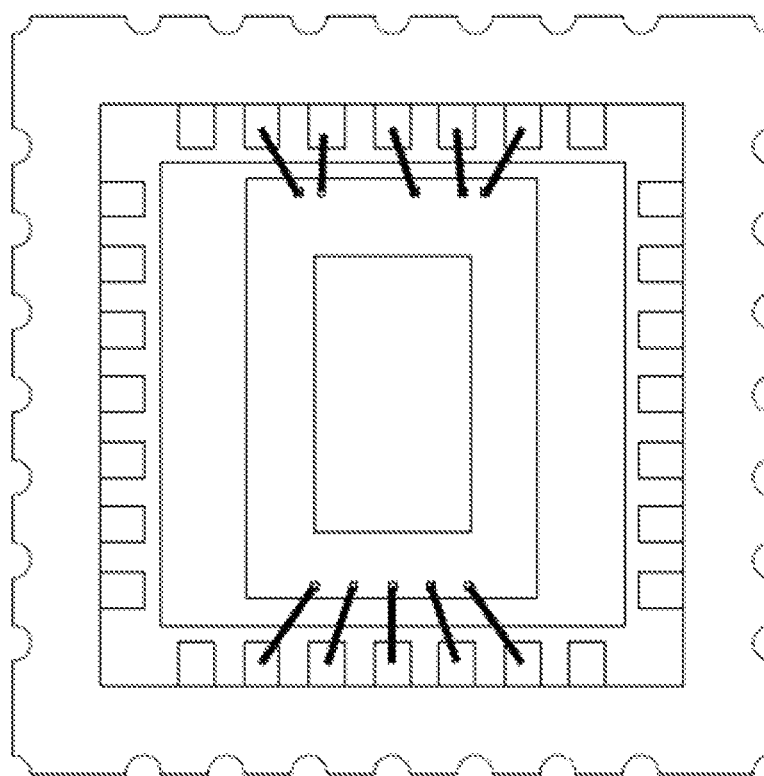

FIGS. 10A and 10B illustrate a top view and a cross-sectional view, respectively, of a conventional, prior art packaged imaging sensor device. It will be appreciated that the connector 206 of the disclosure provides significant advantages over a conventional package for an image sensor. A common method of packaging silicon die comprising an imaging sensor is illustrated. It will be appreciated that the ceramic package has a glass lid to protect the die and the wire bonds as illustrated. Conventional packages are optimized to keep height of the image sensor to a minimum, but the footprint of the image sensor is very large in comparison to the footprint of the image sensor disclosed herein. Due to the mechanical constraints of being located within a tip or distal end of an endoscope or other application where space is constrained, a large footprint is unworkable or undesirable. Conventional packages for an image sensor are optimized for a surface-mount solder process to attach the PCBA, which has local image processing hardware and circuitry (e.g., image processing hardware and circuitry on the same PCBA as the image sensor), but such a configuration may be difficult to connect to a wire harness.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

In the foregoing Detailed Description of the Disclosure, various features of the disclosure may have been grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

What is claimed is:

1. A surgical scope for providing an image in a light deficient environment comprising:
   a tubular member comprising a proximal portion and a distal portion;
   a connector assembly that is located at the distal portion of the tubular member and comprising a first end, a second end, and a plurality of electrical connectors;
   a printed circuit board; and
   an image sensor;
   wherein the image sensor is connected to the connector assembly at the first end of said connector assembly,
   wherein a portion of the printed circuit board is received into the connector assembly at the second end of said connector assembly, such that the connector assembly attaches the image sensor at the distal portion of the tubular member and electrically connects the image sensor to the printed circuit board via the plurality of electrical connectors, thereby providing electrical communication between the image sensor and the printed circuit board,
   wherein the connector assembly comprises a cavity comprising a sidewall at the first end, and
   wherein the image sensor is located within the cavity such that the sidewall of said cavity surrounds at least a portion of the image sensor, thereby protecting the image sensor and electrical connectors.

2. The surgical scope of claim 1, wherein the connector assembly attaches the image sensor within the tubular member in a vertical and perpendicular orientation with respect to the printed circuit board.

3. The surgical scope of claim 2, wherein the printed circuit board is attached perpendicularly out of the center of and with respect to the image sensor.

4. The surgical scope of claim 2, wherein the printed circuit board is attached perpendicularly off of an edge of and with respect to the image sensor.

5. The surgical scope of claim 1, wherein the image sensor comprises a plurality of electrical pads that are electrically attached to the plurality of electrical connectors via wire bonds.

6. The surgical scope of claim 1, wherein the image sensor is electrically attached to one of the plurality of electrical connectors via an electrically conductive adhesive.

7. The surgical scope of claim 6, wherein the image sensor is electrically attached to the plurality of electrical connectors via wire bonds; wherein the image sensor comprises a silicon die; and wherein the electrically conductive adhesive is placed in controlled locations of the connector assembly to electrically connect a backside of the silicon die to a ground in the connector assembly.

8. The surgical scope of claim 1, wherein the image sensor is backside illuminated and comprises a plurality of electrical pads that are soldered to the plurality of electrical connectors of the connector assembly to thereby electrically attach the image sensor to the connector assembly.

9. The surgical scope of claim 1, wherein the image sensor is located above a plane of the electrical connectors at the first end of the connector assembly, such that the electrical connectors are located underneath the image sensor.

10. The surgical scope of claim 1, wherein the image sensor comprises a pixel array that is located above a plane of the electrical connectors at the first end of the connector assembly.

11. The surgical scope of claim 1, wherein the image sensor comprises a pixel array that is located on the same plane as the electrical connectors at the first end of the connector assembly.

12. The surgical scope of claim 1, wherein the image sensor comprises a pixel array that is located beneath a plane of the electrical connectors at the first end of the connector assembly.

13. The surgical scope of claim 1, wherein the second end of the connector assembly comprises a first slot for receiving the printed circuit board therein; and wherein the printed circuit board is held in the first slot via a bias force.

14. The surgical scope of claim 13, wherein the plurality of electrical connectors extend into the first slot, such that when the printed circuit board is located within the first slot the electrical connectors of the connector assembly are in electrical communication with corresponding electrical connectors on the printed circuit board.

15. A system for providing an image in a light deficient environment, the system comprising:
   a surgical scope comprising a tubular member comprising a proximal portion and a distal portion;
   a light source;
   a camera control unit; and
   a display;
   wherein the surgical scope comprises:
     a connector assembly that is located at the distal portion of the tubular member and comprising a first end, a second end, and a plurality of electrical connectors;
     a printed circuit board; and
     an image sensor;
   wherein the image sensor is connected to the connector assembly at the first end of said connector assembly,
   wherein a portion of the printed circuit board is received into the connector assembly at the second end of said connector assembly, such that the connector assembly attaches the image sensor at the distal portion of the tubular member and electrically connects the image sensor to the printed circuit board via the plurality of electrical connectors, thereby providing electrical communication between the image sensor and the printed circuit board,
   wherein the connector assembly comprises a cavity comprising a sidewall at the first end, and
   wherein the image sensor is located within the cavity such that the sidewall of said cavity surrounds at least a portion of the image sensor, thereby protecting the image sensor and electrical connectors.

16. The system of claim 15, wherein the connector assembly attaches the image sensor within the tubular member in a vertical and perpendicular orientation with respect to the printed circuit board.

17. The system of claim 16, wherein the printed circuit board is attached perpendicularly out of the center of and with respect to the image sensor.

18. The system of claim 16, wherein the printed circuit board is attached perpendicularly off of an edge of and with respect to the image sensor.

19. The system of claim 15, wherein the image sensor comprises a plurality of electrical pads that are electrically attached to the plurality of electrical connectors via wire bonds.

20. The system of claim 15, wherein the image sensor is electrically attached to one of the plurality of electrical connectors via an electrically conductive adhesive.

21. The system of claim 20, wherein the image sensor is electrically attached to the plurality of electrical connectors via wire bonds; wherein the image sensor comprises a silicon die; and wherein the electrically conductive adhesive is placed in controlled locations of the connector assembly to electrically connect a backside of the silicon die to a ground in the connector assembly.

22. The system of claim 15, wherein the image sensor is backside illuminated and comprises a plurality of electrical pads that are soldered to the plurality of electrical connectors of the connector assembly to thereby electrically attach the image sensor to the connector assembly.

23. The system of claim 15, wherein the image sensor is located above a plane of the electrical connectors at the first end of the connector assembly, such that the electrical connectors are located underneath the image sensor.

24. The system of claim 15, wherein the image sensor comprises a pixel array that is located above a plane of the electrical connectors at the first end of the connector assembly.

25. The system of claim 15, wherein the image sensor comprises a pixel array that is located on the same plane as the electrical connectors at the first end of the connector assembly.

26. The system of claim 15, wherein the image sensor comprises a pixel array that is located beneath a plane of the electrical connectors at the first end of the connector assembly.

27. The system of claim 15, wherein the second end of the connector assembly comprises a first slot for receiving the printed circuit board therein; and wherein the printed circuit board is held in the first slot via a bias force.

28. The system of claim 27, wherein the plurality of electrical connectors extend into the first slot, such that when the printed circuit board is located within the first slot the electrical connectors of the connector assembly are in electrical communication with corresponding electrical connectors on the printed circuit board.

* * * * *